US00PP20196P2

(12) United States Plant Patent
Fuess

(10) Patent No.: US PP20,196 P2
(45) Date of Patent: Aug. 4, 2009

(54) ***CHRYSANTHEMUM* PLANT NAMED 'EMPIRE EMMA'**

(50) Latin Name: *Chrysanthemum×morifolium*
Varietal Denomination: Empire Emma

(76) Inventor: Janet S. Fuess, 22 Country Club Dr., New York Mills, NY (US) 13417

( * ) Notice: Subject to any disclaimer, the term of this patent is extended or adjusted under 35 U.S.C. 154(b) by 0 days.

(21) Appl. No.: 12/214,225

(22) Filed: Jun. 16, 2008

(51) Int. Cl.
*A01H 5/00* (2006.01)

(52) U.S. Cl. ..... Plt./290

(58) Field of Classification Search ..... Plt./290
See application file for complete search history.

*Primary Examiner*—Annette H Para
(74) *Attorney, Agent, or Firm*—C. A. Whealy

(57) ABSTRACT

A new and distinct cultivar of *Chrysanthemum* plant named 'Empire Emma', characterized by its compact, upright and mounding plant habit; freely branching habit; uniform and freely flowering habit; decorative-type inflorescences with light bronze-colored ray florets; and natural season flowering about October 11$^{th}$ in the Northern Hemisphere.

1 Drawing Sheet

Botanical designation: *Chrysanthemum×morifolium.*
Cultivar denomination: 'Empire Emma'.

BACKGROUND OF THE INVENTION

The present invention relates to a new and distinct cultivar of *Chrysanthemum* plant, botanically known as *Chrysanthemum×morifolium,* commercially grown as a perennial garden *Chrysanthemum,* and hereinafter referred to by the name 'Empire Emma'.

The objective of the breeding program is to create new perennial garden-type *Chrysanthemum* cultivars having uniformly rounded plant habit, inflorescences with desirable inflorescence forms, attractive floret colors and good garden performance.

The new *Chrysanthemum* originated from a cross-pollination made by the Inventor in October, 2002, in New York Mills, N.Y. of *Chrysanthemum×morifolium* 'Empire Harmony', disclosed in U.S. Plant Pat. No. 11,830, as the female, or seed, parent with a proprietary selection of *Chrysanthemum×morifolium* identified as code number G01-12, not patented, as the male, or pollen, parent. The new *Chrysanthemum* was discovered and selected by the Inventor as a single flowering plant within the progeny of the stated cross-pollination in a controlled greenhouse environment in New York Mills, N.Y. in September, 2003.

Asexual reproduction of the new *Chrysanthemum* by vegetative cuttings was first conducted in a controlled greenhouse environment in New York Mills, N.Y. in October, 2003. Asexual reproduction by cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Empire Emma'. These characteristics in combination distinguish 'Empire Emma' as a new and distinct garden *Chrysanthemum* cultivar:

1. Compact, upright and mounded plant habit.
2. Freely branching habit.
3. Uniform and freely flowering habit.
4. Decorative-type inflorescences.
5. Light bronze-colored ray florets.
6. Natural season flowering occurs about October 11$^{th}$ in the Northern Hemisphere.

In side-by-side comparisons conducted in New York Mills, N.Y., plants of the new *Chrysanthemum* differed from plants of the female parent, 'Empire Harmony', in the following characteristics:

1. Plants of the new *Chrysanthemum* were more mounded than plants of 'Empire Harmony'.
2. Plants of the new *Chrysanthemum* flowered two weeks after plants of 'Empire Harmony' when grown under natural season conditions.
3. Plants of the new *Chrysanthemum* had larger inflorescences than plants of 'Empire Harmony'.

In side-by-side comparisons conducted in New York Mills, N.Y., plants of the new *Chrysanthemum* differed from plants of the male parent selection in the following characteristics:

1. Plants of the new *Chrysanthemum* flowered one week later than plants of the male parent selection.
2. Plants of the new *Chrysanthemum* had slightly larger inflorescences than plants of the male parent selection.
3. Plants of the new *Chrysanthemum* and the male parent selection differed in ray floret color as plants of the male parent selection had pink-colored ray florets.

Plants of the new *Chrysanthemum* can be compared to plants of *Chrysanthemum×morifolium* 'Denise', disclosed in U.S. Plant Pat. No. 8,178. In side-by-side comparisons conducted in New York Mills, N.Y., plants of the new *Chrysan-*

*themum* differed from plants of 'Denise' in the following characteristics:

1. Plants of the new *Chrysanthemum* were smaller and more mounded than plants of 'Denise'.
2. Plants of the new *Chrysanthemum* flowered five days later than plants of 'Denise' when grown under natural season conditions.
3. Plants of the new *Chrysanthemum* had slightly smaller inflorescences than plants of 'Denise'.

Plants of the new *Chrysanthemum* can be compared to plants of *Chrysanthemum×morifolium* 'Gedi One Pra', disclosed in U.S. Plant Pat. No. 13,892. In side-by-side comparisons conducted in New York Mills, N.Y., plants of the new *Chrysanthemum* differed from plants of 'Gedi One Pra' in the following characteristics:

1. Plants of the new *Chrysanthemum* were smaller than plants of 'Gedi One Pra'.
2. Plants of the new *Chrysanthemum* flowered one week earlier than plants of 'Gedi One Pra' when grown under natural season conditions.
3. Plants of the new *Chrysanthemum* had larger inflorescences than plants of 'Gedi One Pra'.
4. Ray florets of plants of the new *Chrysanthemum* resisted fading longer than ray florets of plants of 'Gedi One Pra'.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph at the bottom of the sheet comprises a side perspective view of a typical flowering plant of 'Empire Emma' grown in a container.

The photograph at the top of the sheet is a close-up view of typical inflorescences of 'Empire Emma'.

DETAILED BOTANICAL DESCRIPTION

The aforementioned photographs and following observations and measurements describe plants grown in New York Mills, N.Y. during the late spring and summer in a polycarbonate-covered greenhouse and under conditions and practices which approximate those generally used in commercial garden *Chrysanthemum* production. During the production of the plants, day temperatures averaged 32° C. and night temperatures averaged 21° C. Plants were grown in 15-containers under short day/long night conditions. Plants were eleven weeks from planting when the photographs and description were taken. In the following description, color references are made to The Royal Horticultural Society Colour Chart, 1995 Edition, except where general terms of ordinary dictionary significance are used.

Botanical classification: *Chrysanthemum×morifolium* 'Empire Emma'.

Parentage:

*Female, or seed, parent.*—*Chrysanthemum×morifolium* 'Empire Harmony', disclosed in U.S. Plant Pat. No. 11,830.

*Male, or pollen, parent.*—Proprietary selection of *Chrysanthemum×morifolium* identified as code number G01-12, not patented.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Perennial decorative-type garden *Chrysanthemum.* Compact, upright and mounded plant habit. Freely branching habit, about five lateral branches each with multiple secondary branches; pinching is not required; dense and full plant habit. Strong and vigorous growth habit.

*Plant height.*—About 15 cm.

*Plant width.*—About 23 cm.

*Lateral branches.*—Length: About 14.5 cm. Diameter: About 6 mm. Internode length: About 1.4 cm. Strength: Strong. Texture: Pubescent; longitudinally ridged. Color: Close to 147B.

*Leaves.*—Arrangement: Alternate, simple. Length: About 6.3 cm. Width: About 5.4 cm. Apex: Broadly acute to mucronate. Base: Truncate with attenuate tendencies. Margin: Palmately lobed, sinuses between lateral lobes mostly parallel. Texture, upper and lower surfaces: Pubescence; veins prominent on lower surface. Color: Developing foliage, upper surface: Close to 147A. Developing foliage, lower surface: Close to 137B. Fully expanded foliage, upper surface: Close to 147A; venation, close to 147C. Fully expanded foliage, lower surface: Close to 147B; venation, close to 147C. Petiole: Length: About 1.8 cm. Diameter: About 3 mm. Texture, upper and lower surfaces: Pubescent. Color, upper and lower surfaces: Close to 147B.

Inflorescence description:

*Appearance.*—Decorative-type inflorescence form with elliptical-shaped ray florets. Inflorescences borne on terminals above foliage. Disc and ray florets arranged acropetally on a capitulum. Inflorescences faintly fragrant.

*Flowering response.*—Under natural season conditions, plants flower about October $11^{th}$ in the Northern Hemisphere.

*Postproduction longevity.*—Inflorescences maintain good color and substance for about three weeks in an outdoor nursery. Inflorescences persistent.

*Quantity of inflorescences.*—About 28 inflorescences develop per lateral branch.

*Inflorescence bud.*—Height: About 1.5 cm. Diameter: About 1.4 cm. Shape: Oblate. Color: Close to 160A.

*Inflorescence size.*—Diameter: About 5.8 cm. Depth (height): About 2.6 cm. Disc diameter: About 5 mm. Receptacle diameter: About 2.1 cm. Receptacle height: About 7 mm. Receptacle color: Close to 147A.

*Ray florets.*—Shape: Elliptical; partially quilled. Orientation: Initially upright, then about 90° from vertical. Aspect: Initially incurved, then mostly flat; apices reflex with development. Length: About 2.6 cm. Width: About 8 mm. Apex: Obtuse to shallowly emarginate. Base: Acute. Margin: Entire. Texture, upper and lower surfaces: Smooth, glabrous; velvety; longitudinally ribbed. Number of ray florets per inflorescence: About 274 arranged in about 18 whorls. Color: When opening, upper surface: Close to 160A. When opening, lower surface: Close to 160B. Fully opened, upper surface: Close to 162A; color becoming closer to 162C with development. Fully opened, lower surface: Close to 162C; color becoming closer to 162D with development.

*Disc florets.*—Shape: Tubular, elongated. Length: About 4 mm. Diameter: About 1 mm. Number of disc florets per inflorescence: About 120. Color, immature and mature: Apex: Close to 7B. Mid-section: Close to 8B. Base: Close to 157D.

*Phyllaries.*—Number of phyllaries per inflorescence: About 38 arranged in about three or four whorls. Length: About 9 mm. Width: About 2.5 mm. Shape: Narrowly elliptical. Apex: Acute. Base: Truncate. Texture, upper surface: Smooth, glabrous. Texture, lower surface: Pubescent. Color, upper surface: Close to 146B. Color, lower surface: Close to 147B.

*Peduncles.*—Length, terminal peduncle: About 2.6 cm. Length, fourth peduncle: About 5 cm. Diameter, terminal peduncle: About 3.5 mm. Angle: Mostly upright to 45° from vertical. Strength: Strong. Texture: Pubescent. Color: Close to 191A.

*Reproductive organs.*—Androecium: Not observed. Gynoecium: Pistil length: About 6 mm. Stigma shape: Bi-parted. Stigma color: Close to 5A. Style length: About 4 mm. Style color: Close to 145D. Ovary color: Close to 157D.

*Seed/fruit.*—Seed and fruit production has not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and will overwinter in USDA Zones 5 and higher; plants of the new *Chrysanthemum* have been observed to tolerate high temperature of about 38° C.

It is claimed:

1. A new and distinct *Chrysanthemum* plant named 'Empire Emma' as illustrated and described.

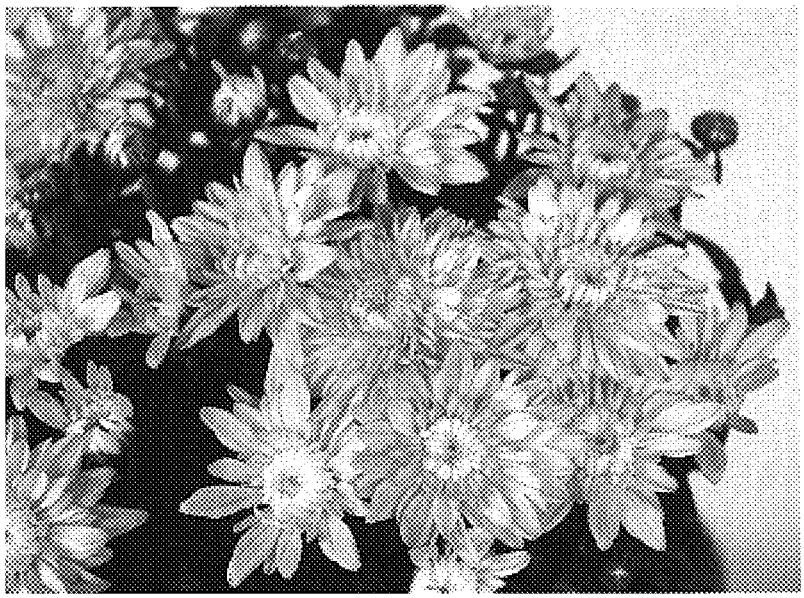
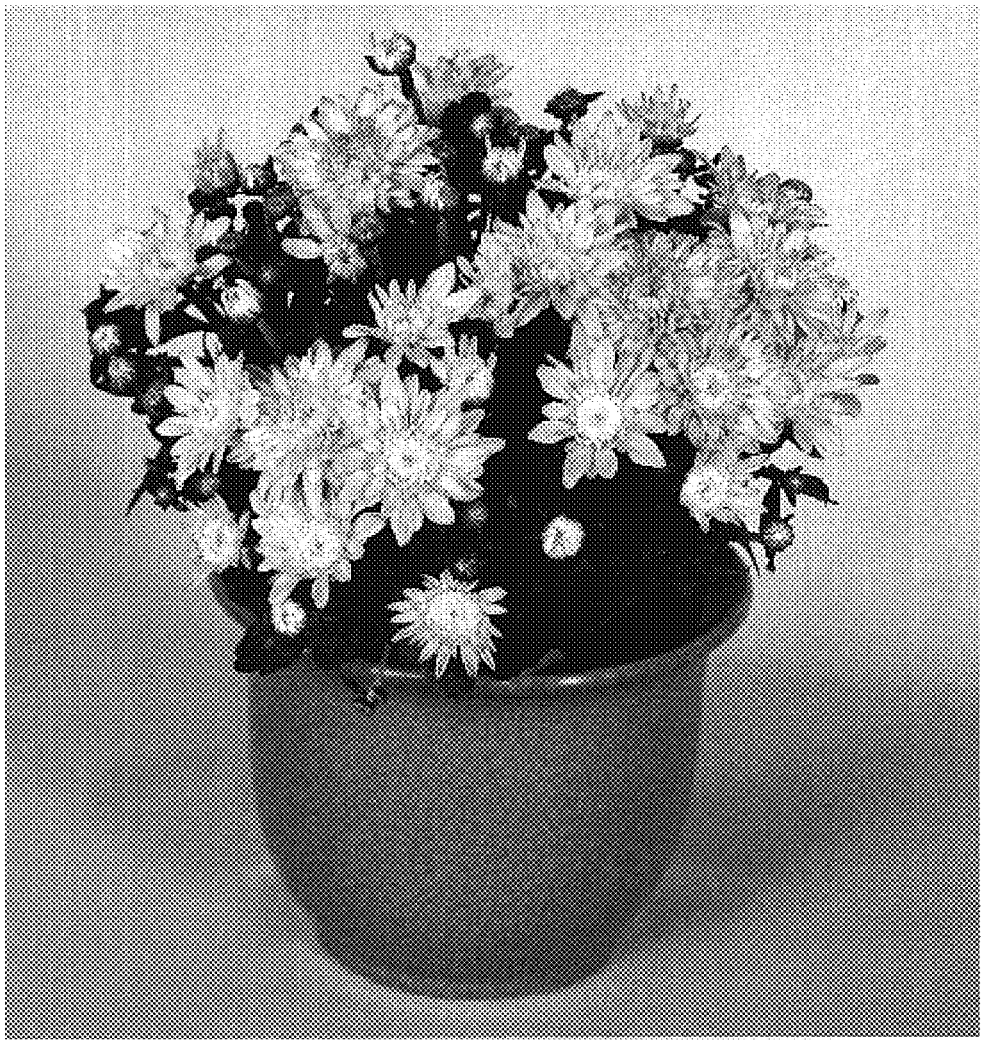

* * * * *